United States Patent
Hassler, Jr. et al.

(10) Patent No.: US 7,601,162 B2
(45) Date of Patent: Oct. 13, 2009

(54) ACTUATOR FOR AN IMPLANTABLE BAND

(75) Inventors: William L. Hassler, Jr., Cincinnati, OH (US); Daniel F. Dlugos, Jr., Morrow, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 354 days.

(21) Appl. No.: 11/036,460

(22) Filed: Jan. 14, 2005

(65) Prior Publication Data

US 2006/0161186 A1     Jul. 20, 2006

(51) Int. Cl.
*A61B 17/132* (2006.01)

(52) U.S. Cl. .................... 606/151; 606/202; 606/203

(58) Field of Classification Search ............. 606/151, 606/157, 202, 207, 208, 120, 203; 128/DIG. 20, 128/DIG. 25
See application file for complete search history.

(56) References Cited

U.S. PATENT DOCUMENTS

| | | | |
|---|---|---|---|
| 3,570,495 A * | 3/1971 | Wright ................... 606/202 |
| 3,840,018 A | 10/1974 | Heifetz |
| 4,201,218 A * | 5/1980 | Feldman et al. ............ 607/112 |
| 4,256,094 A * | 3/1981 | Kapp et al. ................. 601/152 |
| 4,592,339 A | 6/1986 | Kuzmak et al. |
| 4,634,443 A * | 1/1987 | Haber ..................... 600/31 |
| 4,702,235 A * | 10/1987 | Hong ..................... 602/13 |
| 4,898,585 A | 2/1990 | Borsanyi et al. |
| 5,241,965 A * | 9/1993 | Mick ....................... 600/526 |
| 5,383,893 A * | 1/1995 | Daneshvar ................. 606/201 |
| 5,449,368 A * | 9/1995 | Kuzmak .................... 606/157 |
| 6,067,991 A | 5/2000 | Forsell |
| 6,210,347 B1 | 4/2001 | Forsell |
| 6,432,040 B1 | 8/2002 | Meah |
| 6,461,292 B1 | 10/2002 | Forsell |
| 6,470,892 B1 * | 10/2002 | Forsell ...................... 128/899 |
| 6,478,745 B2 * | 11/2002 | Nakagawa et al. .......... 600/499 |
| 6,485,462 B1 | 11/2002 | Kriesel |
| 6,547,801 B1 * | 4/2003 | Dargent et al. ............. 606/157 |
| 6,855,115 B2 | 2/2005 | Fonseca et al. |

(Continued)

FOREIGN PATENT DOCUMENTS

EP     1 547 549     6/2005

(Continued)

OTHER PUBLICATIONS

EPO Search Report, Application No. 06250156.4, Mar. 5, 2005, pp. 1-5.

(Continued)

*Primary Examiner*—Anhtuan T Nguyen
*Assistant Examiner*—Ryan J Severson
(74) *Attorney, Agent, or Firm*—Dean Garner (57) ABSTRACT

An actuator having a variable internal volume is mechanically coupled to an adjustable implantable band so as to effect changes in the effective internal perimeter of the band. The actuator may be directly connected to the band, or be connected through a cable. Configurations of the actuator include a series of folds and ridges and bellows. A plurality of actuators may be used in combination with a single band. A clutch mechanism may be included to hold the band in place when not acted upon by the actuators. One end of the actuator may be connected directly to a bidirectional flow device.

20 Claims, 10 Drawing Sheets

U.S. PATENT DOCUMENTS

| | | |
|---|---|---|
| 7,351,240 B2 | 4/2008 | Hassler, Jr. et al. |
| 7,374,565 B2 | 5/2008 | Hassler, Jr. et al. |
| 7,390,294 B2 | 6/2008 | Hassler, Jr. et al. |
| 7,442,165 B2 | 10/2008 | Forsell |
| 7,481,763 B2 | 1/2009 | Hassler, Jr. et al. |
| 2003/0105385 A1 | 6/2003 | Forsell |
| 2003/0136417 A1 | 7/2003 | Fonseca et al. |
| 2004/0260319 A1 | 12/2004 | Egle |
| 2004/0267377 A1 | 12/2004 | Egle |
| 2005/0143765 A1* | 6/2005 | Bachmann et al. .......... 606/157 |
| 2005/0143766 A1 | 6/2005 | Bachmann et al. |
| 2006/0189888 A1 | 8/2006 | Hassler, Jr. et al. |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2008/0221598 A1 | 9/2008 | Dlugos et al. |

FOREIGN PATENT DOCUMENTS

| | | |
|---|---|---|
| EP | 1 600 120 | 11/2005 |
| EP | 1 704 833 | 9/2006 |
| EP | 1 832 253 | 9/2007 |
| EP | 1 967 168 | 9/2008 |
| GB | 1 486 822 | 9/1997 |
| WO | WO 01/51108 A1 | 7/2001 |
| WO | WO 03/061504 | 7/2003 |
| WO | WO 03/105732 | 12/2003 |

OTHER PUBLICATIONS

Examination Report dated Feb. 20, 2007 for Application No. 06250156.

Partial EPO Search Report dated Jan. 13, 2009 for Application No. 08250782.

Extended EPO Search Report dated Apr. 22, 2009 for Application No. 08250782.

* cited by examiner

ACTUATOR FOR AN IMPLANTABLE BAND

FIELD OF THE INVENTION

The present invention relates generally to actuating devices, and more particularly to actuators for use with an implantable constriction member. The invention will be disclosed in connection with, but not limited to, surgically implantable bands for encircling an anatomical passageway, such as gastric bands.

BACKGROUND OF THE INVENTION

Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band.

An implantable band may be utilized in any number of applications within a patient's body where it is desirable to establish and/or vary the size of an orifice or organ. As used herein and in the claims, an implantable band is a band which may be implanted in a position to vary the size of an organ, or an orifice or an anatomical passageway, such as a stomach or lumen.

Depending upon the application, some prior art bands take the form of a flexible, substantially non-extensible band containing an expandable section that is capable of retaining fluids. The expandable section, such as a hollow elastomeric balloon, is typically capable of expanding or contracting, depending upon the volume of fluid contained therein.

Bidirectional flow control is required to increase and decrease the size of the stoma created by the band. Adding or removing saline solution to effect a change in size of the stoma created by an implantable band may be accomplished by us of an implanted bidirectional flow device, such as for example a subcutaneously implanted fluid injection port or bidirectional infuser pump, such as disclosed in U.S. patent application Ser. No. 10/857,315, filed on May 28, 2004, for Thermodynamically Driven Reversible Infuser Pump For Use As A Remotely Controlled Gastric Band, U.S. patent application Ser. No. 10/857,762, filed on May 28, 2004, for Piezo Electrically Driven Bellows Infuser For Hydraulically Controlling An Adjustable Gastric Band, U.S. patent application Ser. No. 10/857,763, filed on May 28, 2004, for Bi-Directional Infuse Pump With Volume Braking For Hydraulically Controlling An Adjustable Gastric Band, and U.S. patent application Ser. No. 10/856,971, filed on May 28, 2004, for Metal Bellows Position Feedback For Hydraulic Control Of An Adjustable Gastric Band, all of which are incorporated herein by reference.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Reference will now be made in detail to the present preferred embodiment of the invention, an example of which is illustrated in the accompanying drawings.

DETAILED DESCRIPTION OF AN EMBODIMENT OF THE INVENTION

In the following description, like reference characters designate like or corresponding parts throughout the several views. Also, in the following description, it is to be understood that terms such as front, back, inside, outside, and the like are words of convenience and are not to be construed as limiting terms. Terminology used in this patent is not meant to be limiting insofar as devices described herein, or portions thereof, may be attached or utilized in other orientations. Referring in more detail to the drawings, the invention will now be described.

Figure 1:
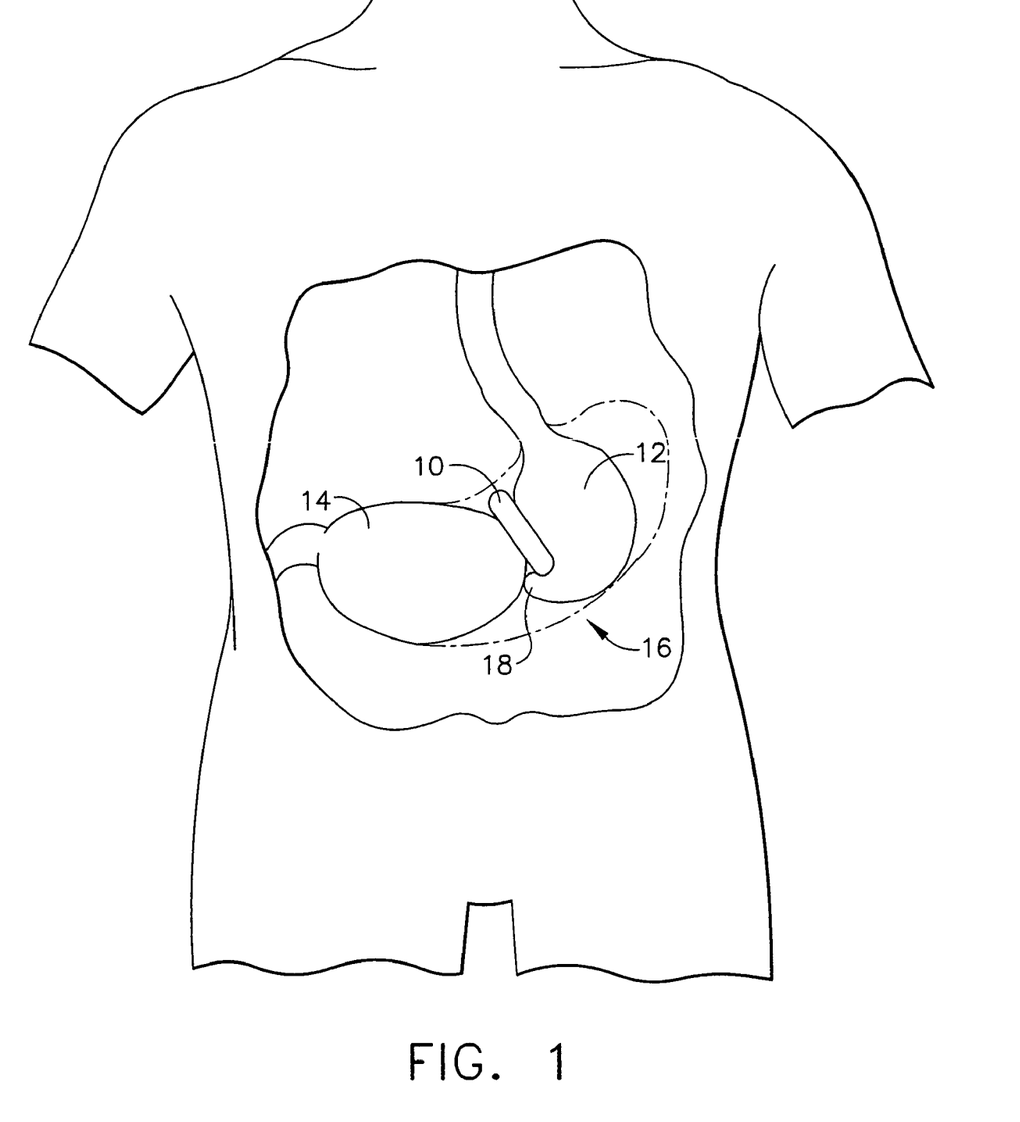
FIG. 1 is a diagrammatic environmental view of a gastric band wrapped around an upper part of a stomach.

Referring to FIG. 1, adjustable gastric band 10 forms an adjustable stoma between upper portion 12 and lower portion 14 of a patients stomach 16. Band 10 is kept in place by attaching its two ends together and extending portion 18 of stomach 16 over the adjustable gastric band 10 by suturing portion 18 to stomach 16. The stoma may be adjusted by varying the effective inner perimeter (which may also referred to as inner diameter, although the shape is not necessarily a circle) of band 10. An actuator is associated with band 10 to vary the inner perimeter. The actuating device may be integral with the band itself or be external thereto.

Figure 2:
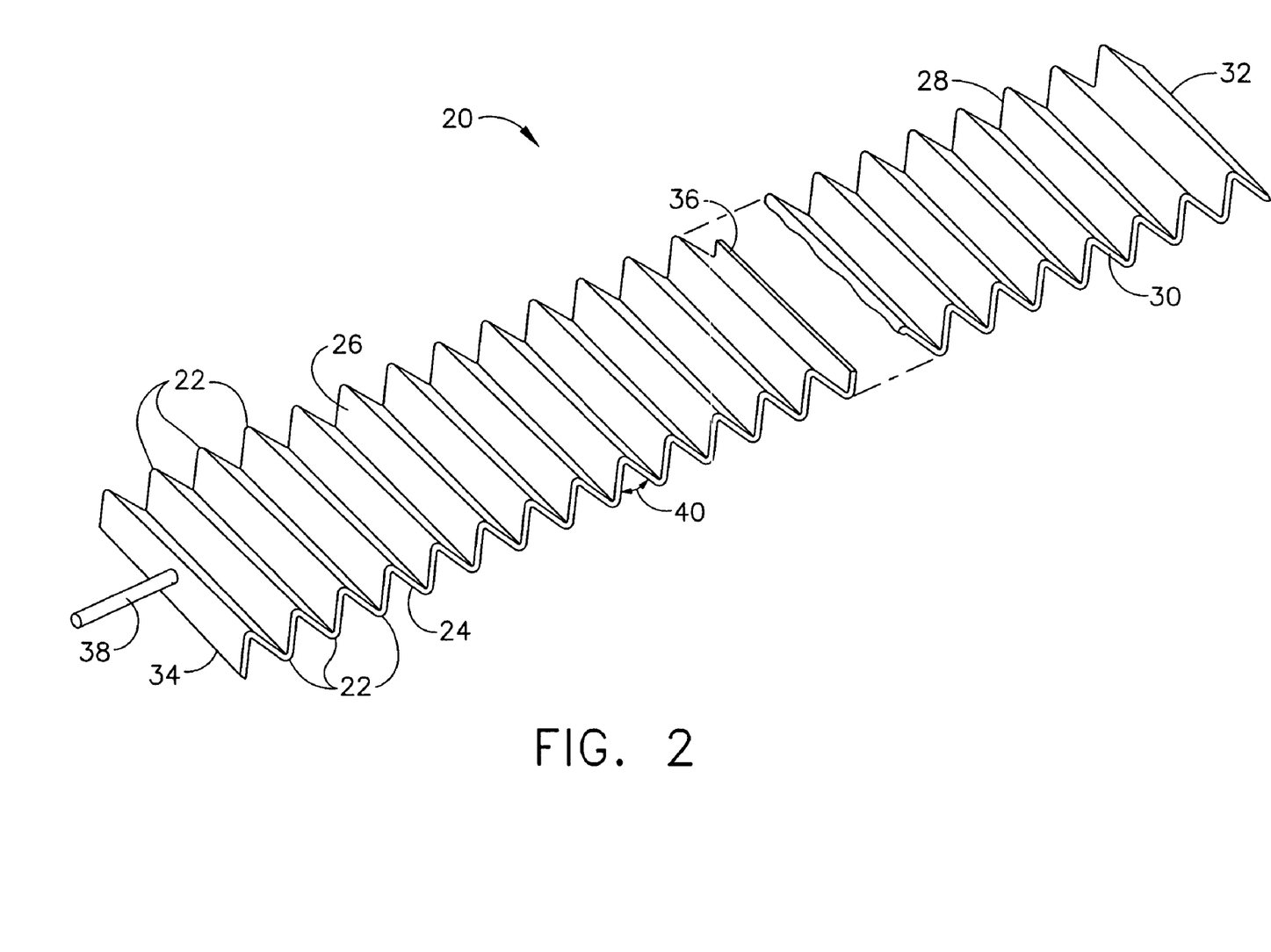
FIG. 2 is a perspective view of an actuator.

FIG. 2 illustrates an embodiment of an actuator which may be used with band 10 to vary the inner perimeter. Actuator 20 is depicted as an elongated member, although any suitable length to width ratio may be used based on the specific needs. Actuator 20 is configured to change shape in response to an increase in internal volume, with the change in shape adapted to vary the size of the stoma. As shown in FIG. 2, actuator 20 is depicted as a corrugated member having a series of folds creating spaced apart ridges 22 on the upper and lower sides of actuator 20. Although the ridges and folds are illustrated as being parallel, and evenly shaped and spaced, they are not required to be.

Actuator 20 comprises first and second sidewalls 24 and 26, sealed to each other along exterior edges 28, 30, 32 and 34 by any suitable method, thereby defining internal cavity 36. For example, exterior edges 28, 30, 32 and 34 may be laser or E-beam welded. Any suitable Actuator 20 includes a fluid port 38 which is in fluid communication with internal cavity 36.

Sidewalls 24 and 26 are made of any suitable biocompatible material having sufficient resilience, strength and fatigue resistance to change the shape of actuator 20 in response to changes in the volume within internal cavity 36, such as CP2 Ti. Additionally, sidewalls 24 and 26 may be made of a material which is MRI safe.

For example, in the embodiment depicted in FIG. 2, sidewalls 24 and 26 may be made of titanium having a thickness of approximately 0.001 to 0.005 inches. Ridges 22 comprise the vertex of included angle 40, and may be rounded to minimize stress concentrations in the material during actuation. In the non-actuated state, actuator 20 is normally compressed, similar to a spring, and included angles 40 may be approximately 30°, or less. When fully actuated, included angles 40 may expand to approximately 80°, thereby producing a strain difference of over 100% of its initial length. Actuator 20 is configured to retract to its normally compressed state when the internal fluid is removed.

In the embodiment depicted, actuator 20 is configured to handle an internal pressure of at least up to approximately 20 psig, which would produce a longitudinal actuation force of at least 1.5 lbf for an actuator of 0.5 inches wide and 0.25 inches high (in the non-actuated state), sufficient to overcome secondary peristalsis pressures of 2 psi.

Figure 3:
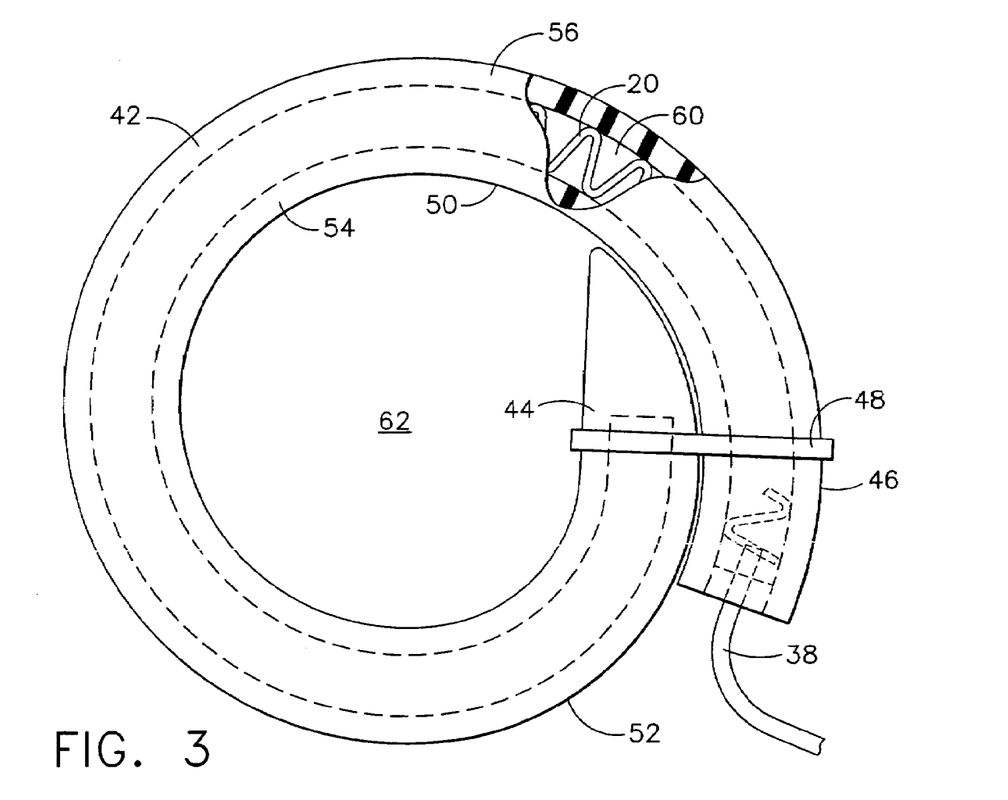
FIG. 3 is a plan view of a gastric band incorporating the actuator of FIG. 2.
Figure 4:
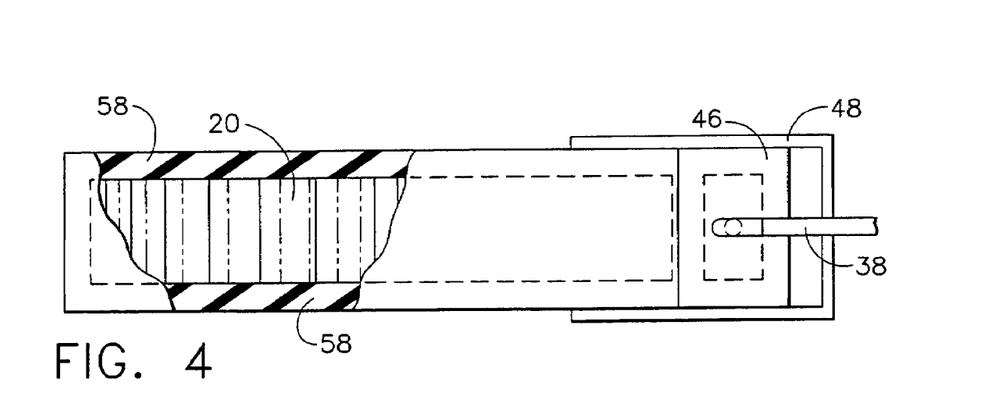
FIG. 4 is a side view of the gastric band of FIG. 3.
Figure 5:
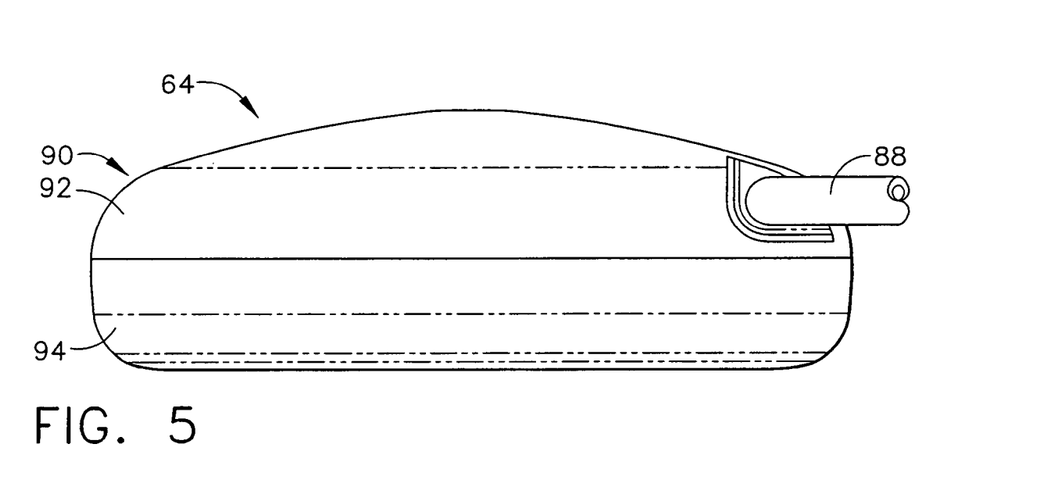
FIG. 5 is a side view of an implantable bidirectional infuser.
Figure 6:
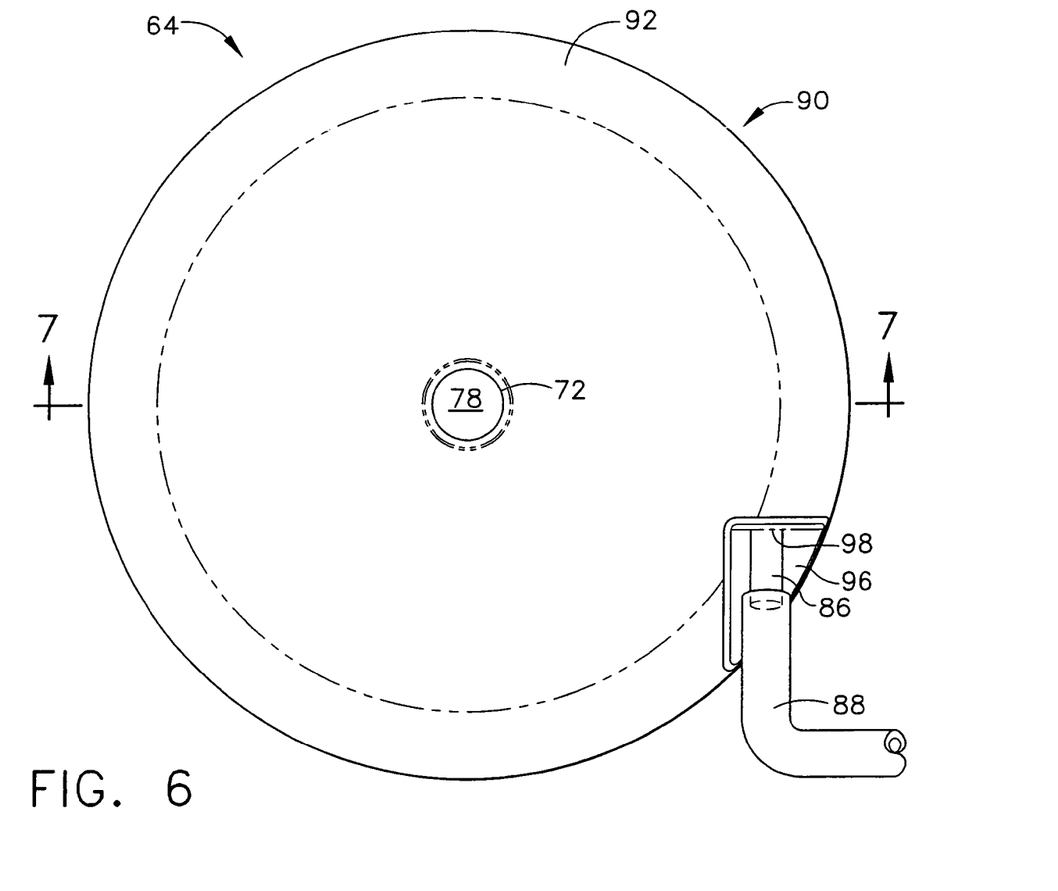
FIG. 6 is a top view of the bidirectional infuser of FIG. 5.

FIGS. 3 and 4 illustrate adjustable band 42 which may be implanted in a position to occlude flow, such as of food or body fluids, through an anatomical passageway, such as a stomach or lumen. In particular, band 42 is depicted as a gastric band to be disposed about a stomach, although it is to be understood that the teachings of the present invention are not limited to gastric bands. Band 42 has first and second opposite ends 44 and 46 which are secured to each other by connecting member 48, with inner band surface 50 at end 46 adjacent outer band surface 52 at end 44. Connecting member 48, which is depicted as a strap but may be of any suitable configuration, may be secured to ends 44 and 46 by any suitable means. At least one end 44 or 46 should not be connected to connecting member 48 prior to implanting band 42. Although ends 44 and 46 overlap, any suitable connecting configuration may be used. For example, ends 44 and 46 may not directly contact each other, with a connecting member extending therebetween. Additionally, for example, inner band surface 50 of each end 44 and 46 may be disposed adjacent each other, extending outwardly from the encircled center area.

In the embodiment depicted, band 42 includes inner side wall 54, outer side wall 56, and transverse side walls 58 which define interior cavity 60. Actuator 20 is disposed within interior cavity 60, with at least fluid port 38 extending therefrom. Band 42 is configured to maintain actuator 20 within interior cavity 60 during actuation. In order to do so, in the embodiment depicted, the portion of actuator 20 adjacent end 34 may be secured within interior cavity 60 adjacent end 46 in any suitable manner. The portion of actuator 20 adjacent end 32 may be secured within interior cavity 60 adjacent end 44.

Band 42 may be made from any suitable biocompatible material having sufficient strength, elasticity and fatigue resistant to accommodate activation and deactivation of actuator 20. In the embodiment, depicted, band 42 is made of a soft compliant silicone material which prevents actuator 20 from causing discomfort to adjacent tissue.

In use, band 42 is first surgically located about the stomach in the appropriate location, and connecting member 48 is then secured to the free one of ends 44 and 46 in any suitable manner. With ends 44 and 46 connected, band 42 encloses area 62 as seen in FIG. 3, the cross sectional area of which depends on the length of actuator 20. End 44 may, but does not have to, terminate in a taper, as shown, to blend smoothly into inner band surface 50.

In FIG. 3, actuator 20 is illustrated in its non-actuated state, having its shortest length, and therefore area 62 is at its minimum. The size of area 62 may be increased by increasing the length of the perimeter defined by inner band surface 50. This may be accomplished by pressurizing internal cavity 36 by introducing fluid through fluid port 38, increasing the included angles 40 thereby increasing the length of actuator 20. With ends 44 and 46 connected together, the length of band 42 therebetween must increase as actuator 20 urges outwardly against outer sidewall 56. The increase in length increases the perimeter defined by inner band surface 50, thus increasing the size of area 62. When the desired size of area 62 is achieved, fluid flow through fluid port 38 ceases and the pressure is maintained, and actuator 20 and band 42 maintain a fixed position.

The actuated state of actuator 20 dictates the largest size of area 62. Upon release of pressure, actuator 20 is configured to return to its non-actuated state having the shortest length, urging inner side wall 54 against the stomach with sufficient force to reduce the size of the stoma.

Band 42 may be configured to coact with actuator 20 using any suitable construction. For example, actuator 20 may be comolded in a band, eliminating the need for interior cavity 60. Actuator 20 may be disposed completely internal within a band, as depicted (except for the fluid port), or may be partially external to the band provided that the surrounding tissue will not be harmed.

Band 42 may also be configured such that the increase in length of actuator 20 causes only end 44 to extend longitudinally, sliding along inner band surface 50 to fill into area 62. In such a configuration, outer sidewall 56 must sufficiently resist longitudinal stretching between ends 44 and 46 to radially restrict band 42 so as to produce extension of end 44, and end 44 must have sufficient elasticity to stretch the required distance past the location of connecting member 48. Operation of such a configuration may be assisted by the growth of connective tissue around band 42 after surgery, channeling band 42.

Thus, band 42 may have any suitable configuration which alone, or in cooperation with surrounding tissue, changes shape in response to the actuation of actuator 20 so as to vary the size of the stoma. Although the configuration of actuator 20 depicted produces in increase in its longitudinal length, actuator 20 may be configured to increase in other dimensions functional to effect the desired size control.

Actuator 20 is preferably configured to have its internal cavity filled in a controllable manner to produce the desired stoma size. It may be connected to any suitable source of fluid pressure, which may be controlled bidirectionally to achieve and maintain the desired size. For example, in the embodiment depicted, actuator 20 may be filled with a fluid, such as saline, and fluid port 38 may be connected by a flexible conduit communicating with a bidirectional fluid device, such as an injection port or a pump, either of which may implanted subcutaneously. With an injection port, the volume of the fluid within actuator 20 may be controlled by inserting a Huber tip needle through the skin into a silicone septum of the injection port. Once the needle is removed, the septum seals against the hole by virtue of the compressive load generated by the septum.

Referring to FIGS. 5, 6, 7 and 8, an implantable bidirectional infuser 64 is illustrated which may be used with actuator 20. Infuser 64 has a rounded lozenge-shape that for clarity is described with respect to the orientation depicted in the figures with what is typically outwardly oriented with respect to the skin of the patient described as upward, as infuser 64 would typically be oriented when placed upon a table.

Infuser device 64 provides bidirectional hydraulic control by holding a variable amount of fluid within bellows accumulator 66 formed from titanium metal bellows 68 that may be expanded and compressed along its longitudinal axis. Bellows bottom plate 70, also formed from titanium, closes off a bottom opening of bellows 68 with top opening 72 substantially sealed by titanium bellows deck plate 74. Infuser device and its components may be made of any suitable biocompatible material, including ductile non-permeable material and MRI safe material.

Figure 7:
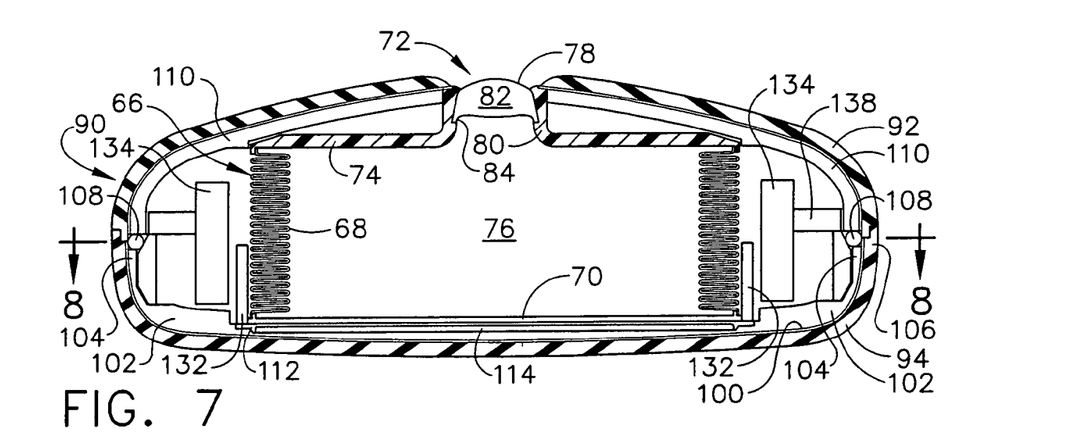
FIG. 7 is a side view in cross section taken along lines 7-7 of FIG. 6 depicting a drum brake assembly released by expanding piezo-electric stack actuators to disengage brake arms of the calipers from a brake drum attached to the metal bellows accumulator which is in an expanded condition.

Fluid communication with selectable internal volume 76 of bellows accumulator 66 is provided by septum 78, provided by central spout 80 that defines top opening 72 and is formed in bellows deck plate 74. Septum 78 is ordinarily closed by polymeric septum seal 82, which may be formed from a silicone material or other biocompatible material and press fit into septum recess 84 having a circular horizontal cross section parallel to top opening 72 in spout 80 and a trapezoidal cross section across the longitudinal axis of spout 80. Septum 78 allows insertion of a syringe into selectable internal volume 76 to add or remove fluid as either a backup capability or during initial installation.

Internal volume 76 of bellows accumulator 66 is in fluid communication with nipple 86 through an access port (not shown) formed in deck plate 74, and is placed in fluid communication with fluid port 38 through flexible conduit 88.

Outer case 90, which is formed of a biocompatible plastic, such as PEEK or polysulfone, includes top shell 92 that mates with bottom shell 94, being attached to one another in any suitable manner, such as by fusing, bonding or interference locking. Tangentially directed recess 96 is formed in top shell 92 includes a catheter hole 98 through which nipple 86 passes and seals against.

A bottom half of thin barrier shell 100 conforms to the inside surface the bottom shell 94 of the outer case 90 and is formed of a material such as titanium that provides a hermetic seal. Inside of the bottom half, a bottom carrier 102, formed of a resin or polymer, conforms to the inside surface of the bottom half thin barrier shell 100 for locating actuating components therein and for providing thermal isolation from outer case 90. Rim 104 of bottom carrier 102 is spaced slightly below the rim 106 of bottom shell 94 and the top circumference of the bottom half of thin barrier enclosure 100.

A top half of the thin barrier enclosure 100 conforms to the inside surface of top shell 92, and is also formed of a material such as titanium that provides a hermetic seal and extends inside of the bottom half of the thin barrier enclosure 100 with a small overlap thereto that may be welded or otherwise affixed (e.g., bonded, fused) together. A titanium-ring 108, inside of this overlapping portion of the top and bottom halves of thin barrier enclosure 100, rests upon rim 104 of bottom carrier 102 and is compressed by top carrier 110 that conforms to the inner surface of the top half of thin barrier shell 100.

Within outer case 90, a propellant cavity 112 is defined exterior to the bellows accumulator 66 and inside of the top and bottom carriers 110, 102 and titanium ring 108. As the bellows accumulator 66 expands, the volume of propellant cavity 112 decreases. Propellant cavity 112 contains a propellant that has both a liquid and gas phase (or saturated condition) at body temperature at approximately 37 degrees C., such as VERTREL CF that would produce a constant gauge pressure of −4 psig. Thus, rather than seeking a propellant that exerts an essentially neutral gauge pressure, a propellant that exerts a negative gauge pressure bias on the metal bellows accumulator 66 allows for thermodynamically driving a metal bellows accumulator 66 by adding heat. Thus, normal negative gauge pressure of the propellant at body temperature is harnessed for expanding the metal bellows accumulator and heating, such as by transcutaneous energy transfer (TET), is used for contracting the metal bellows accumulator 66. TET heating is achieved by inducing eddy currents that dissipate in metal components of the implant as heat. In some applications, such a pressure bias provides a fail-safe condition of the accumulator failing in an expanded condition, releasing pressure in an attached band.

Moving metal bellows accumulator 66 in the opposite direction, collapsing bellows 68, is achieved by adding heat to the propellant, thereby increasing pressure in the propellant cavity 112 the propellant shifts to a gas phase from a liquid phase. This heat may be generated by various means, such as from a stored battery charge, a controlled exothermic reaction, etc. In the illustrative version, this thermodynamic heating is provided by a heat flux element, such as disk-shaped thin film etched foil heater element 114, which also serves as the inductive position sensing coil and is affixed to the bottom carrier 102 opposite the bellows bottom plate 70. The thermal isolation and thermal sink provided by outer case 90, thin barrier enclosure 100, and top and bottom carriers 110, 102 allow efficient adding of heat to the propellant without a significantly raised external temperature of infuser 64 that would cause discomfort or tissue damage. In some applications, more than one heat flux element of the same or different nature may be used.

As an alternative to heating the propellant to thermodynamically actuate the bellows accumulator, heat flux element 114 may instead comprise a thermoelectric cooler, which is a solid state heat pump based on the Peltier Effect. Thus, a propellant is selected that exerts a positive gauge pressure at body temperature, with thermal element 114 thus used to cool the propellant to create a negative gauge pressure to expand bellows accumulator 70. In addition or in the alternative, thermal element 114 may be capable of both heating and cooling, such as is typical with thermoelectric coolers depending upon the direction of current flow. Thus, even greater volume reductions may be achieved in infuser 64 by being able to achieve a wider temperature range within the propellant, and thus a greater differential pressure range upon bellows accumulator 70.

Thermodynamic actuation may be harnessed in combination with various types of braking devices of the bellow accumulator 66, such as a fluid shut-off valve that prevents fluid from entering or exiting the fluid accumulator 66. In particular, it is desirable that the thermodynamic actuation occurs relatively quickly so that the clinician and patient are not inconvenienced, yet braking avoids over-shooting the desired volume. Further, the braking prevents variation in fluid volume between adjustments, such as due to compressive forces on the gastric band 30 or variations in body temperature or offset steady state gauge pressure.

Figure 8:
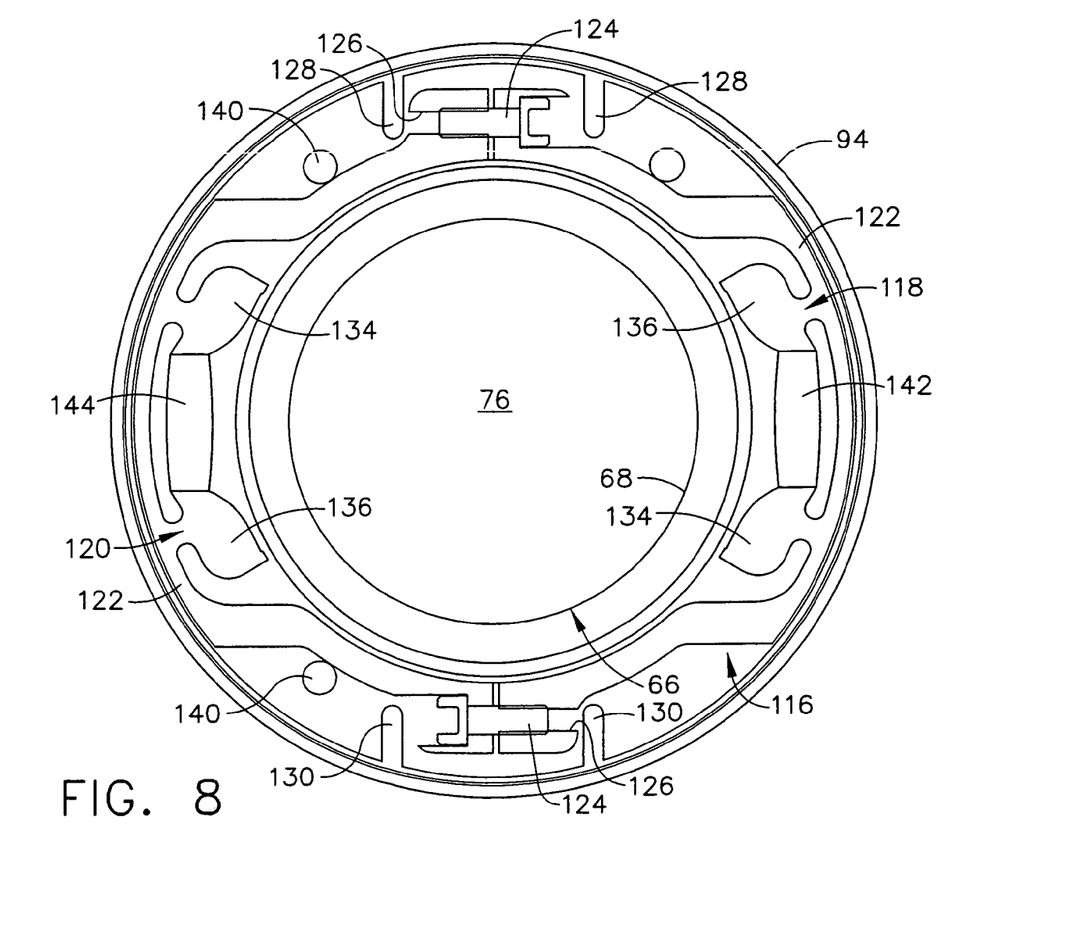
FIG. 8 is a top view in cross section along lines 8-8 of the bidirectional infuser of FIG. 7 taken through calipers and piezo-electric stack actuators of a drum brake assembly.

In the embodiment of exemplary infuser 64 illustrated in FIGS. 5-8, drum brake assembly 116, which is piezo-electrically released, provides long-term volume stability with efficient adjustment. Moreover, the piezo-electrical actuation lends itself to being practically immune from strong external magnetic fields, as may be advantageous for use when exposure to magnetic resonance imaging may occur. In FIGS. 7 & 8, the components of drum brake assembly 116 are shown to include a pair of brake calipers 118, 120, each including semicircular band 122 with an adjustment screw 124 and screw receptacles 126 shaped to receive adjustment screw 124 from the other caliper. A pair of rocker arms 134, 136 on each caliper 118, 120 project inwardly and are spaced apart to receive respectively a piezoelectric stack actuator 142, 144. The assembled calipers 118, 120 are set upon the bottom carrier 102 encompassing the bellows accumulator 66. In particular, cylindrical brake drum 132 is circumferentially attached around bellows bottom plate 70 with its longitudinal length surrounding a lower portion of bellows 68. This longitudinal length is selected such that bellows 68 of bellows accumulator 66 is allowed to fully collapse before brake drum 132 contacts top carrier 110.

As seen in FIGS. 7 & 8, rocker arms 134, 136 are spaced away from the underlying bottom carrier 102 and overlying circuit board 138 to allow slight horizontal deflection into and away from engagement with brake drum 132. Specifically, stand-off posts 140, integral to bottom carrier 102, support circuit board 138 and the portion of bottom carrier 102 proximal to rocker arms 134, 136 and are slightly recessed to avoid contact. The respective screws 124 and screw receptacles 126 of calipers 118, 120 are held in engagement with another by the two pairs of partitions 128, 130 that extend upwardly from bottom carrier 102. The longitudinal length of brake drum 132 and the height and positioning of rocker arms 134, 136 are selected such that brake drum 132 presents an engaging surface to rocker arms 134, 136 through the range of volumes of bellows accumulator 66.

In use, bidirectional infuser 64 is attached to the other end of flexible conduct 88 for selectively providing or withdrawing this fluid from actuator 20 for hydraulic control thereof. In particular, metal bellows accumulator 66 has an initial volume that is based on the degree to which its bellows 68 is collapsed inside of outer case 90. This volume is maintained by drum brake assembly 116 that includes calipers 118, 120 that each inwardly present rocker arm 134, 136 to engage the brake drum 132. To adjust the volume, TET power and telemetry commands are communicated from a primary coil to infuser 64. The primary coil is controlled by a programmer, with both being external to the patient. Circuit board 138 responds to received power and instructions by actuating the two piezo-electric stack actuators 142, 144, each located between a respective pair of rocker arms 134, 136. The slight growth in length spreads the pair of rocker arms 134, 136, disengaging brake drum 132. Circuit board 138 monitors the volume of metal bellows accumulator 66 via position sensing coil 114 and deactivates piezo-electric stack actuators 142, 144 when the desired volume is reached. With the use of incompressible fluid, sensing coil 114 thus may be used to indicate the length of actuator 20, and concomitantly the size of the stoma opening.

Depending on whether the propellant is positively or negatively biasing metal bellows accumulator 66 at body temperature and the desired direction of volume change, circuit board 138 adjusts the temperature of the propellant in propellant cavity 136 by activating thermal element 114 attached to bottom carrier 102 inside of outer case 90. This thermal heating may be achieved through TET eddy current heating and/or using heating element 114. For a negatively biased propellant, a thin film heater (e.g., inductive, resistive, Peltier effect) thus increases the pressure to collapse bellows accumulator 66, with the reverse achieved by merely releasing drum brake assembly 132 after the propellant has cooled to body temperature. Alternatively, for a positively biased propellant at body temperature, a thermo-electric cooler (e.g., Peltier effect) is activated to expand bellow accumulator 66, with the reverse achieved by merely releasing drum brake assembly 132 after the propellant has warmed to body temperature. Thermal isolation of the propellant and heat flux element 114 from the patient by the heat sink and insulative properties of the bidirectional infuser device avoids discomfort and tissue damage while still presenting a desirable small volume.

Internal cavity 36 is relatively small, and only a small amount of incompressible fluid is required to actuate actuator 20 to its full length. For example, actuator 20 as depicted herein, may require only 0.5 mL of liquid to be fully extended. Thus, an actuator constructed in accordance with the teaching of the present invention requires significantly less fluid to achieve a desired opening size than previously required to actuate typical silicon balloon type bands. The reduction in necessary fluid volume enables the size and weight of the bidirectional flow device for driving the fluid to be greatly reduced. Accordingly, a more compact, lightweight band can be created. In addition, the embodiments described herein can be formed entirely from non-ferromagnetic materials, enabling the implanted assembly to be MRI safe.

FIGS. 9, 10, 11 and 12 illustrate another embodiment of an actuator, in conjunction with another embodiment of an adjustable band. Band 148 includes actuators 150 and 152, which are configured similar to actuator 20, except that each lacks a fluid port, the internal cavity of each actuator 150 and 152 being completely sealed without a fluid port. Since actuators 150 and 152 are identical to each other, only actuator 150 will be discussed. Actuator 150 is actuated by an increase of pressure within its internal cavity. But instead of relying on an external source of fluid pressure, actuator 150 is filled with a two phase medium, such as a propellant. For example, Vertrel CF may be used. Thus, an injection port and a bidirectional infuser are unnecessary.

Figure 9:
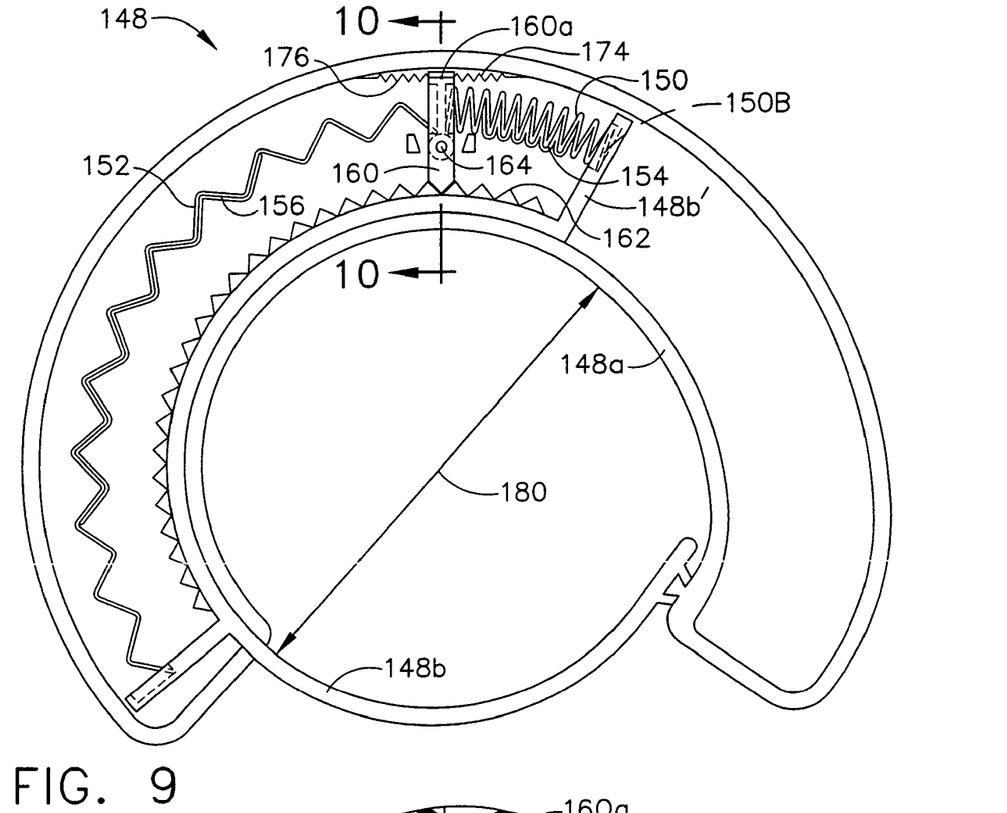
FIG. 9 is a plan view of another embodiment of a band, depicting another embodiment of an actuator.
Figure 10:
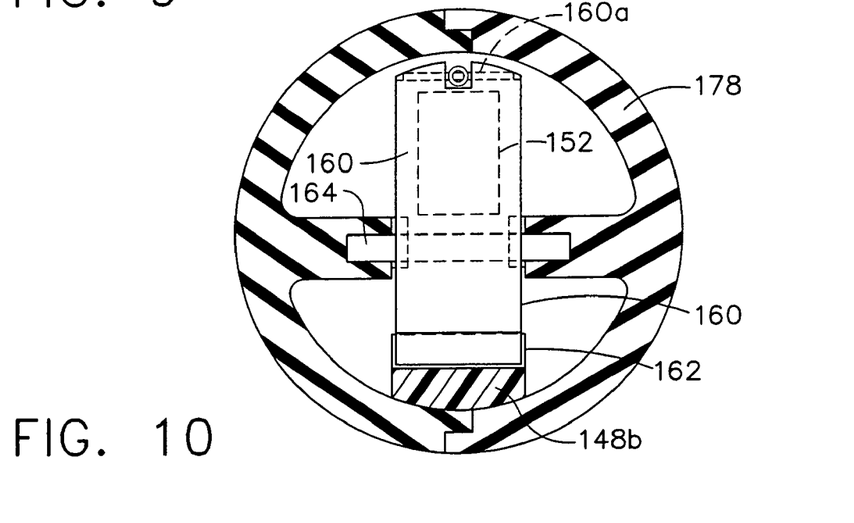
FIG. 10 is a side view in cross section taken along line 10-10 of FIG. 9.

In order to effect the phase change and expansion of the propellant, thermal element 154 (156 for actuator 152) is disposed adjacent actuator 150. In the embodiment depicted, thermal element 154 is a thin film Kapton heater which is attached to a surface of actuator 150. Wires (not shown) extend from element 154, to a controller (not shown) for selectively applying an electrical signal to element 154. In the embodiment depicted, when energized, element 154 produces sufficient heat to warm the two phase medium within the internal cavity of actuator 150, causing the medium to begin changing phase from liquid to gas, thereby increasing the pressure within actuator 150. Actuator 150 is configured to change shape in response to this increase in internal pressure, with the change in shape adapted to vary the size of the stoma.

In the embodiment depicted, actuator 150 lengthens in response to an increase in pressure. A control may measure the change in capacitance of actuator 150 to determine its length. The self capacitance of actuator 150 will vary as it lengthens. Capacitance change may be detected by incorporating actuator 150 into an LC circuit and the frequency variations of an AC signal in the circuit can be compared to a reference frequency to detect the amount of expansion. It is noted that the expansion of actuator 20 could be monitored in the same manner, instead of monitoring the position of the bellows, as described above. For example, such as when actuator 20 is actuated by an injection port. Additionally, a self contained actuator, such as actuator 150, may be used in conjunction with any suitable band configuration, such as band 42 described above.

The embodiment of band 148 depicted in FIGS. 9-12 includes a clutch mechanism configured to hold band 148 at a particular size unless acted upon by either actuator 150 or 152. Although any suitable clutch mechanism may be used, FIGS. 9-12 depict pawl 160 which engages ratchet member 162. Pawl 160 is rotatably supported about transverse pivot 164, which separates pawl into upper portion 166 and lower portion 168. Lower portion 168 terminates in an angle 170 which is shaped complementarily to engage notches 172 of ratchet member 162. First ends 150*a* and 152*a* of actuators 150 and 152 are attached to respective sides of upper portion 166 in any suitable manner. Alternatively, actuators 150 and 152 could be configured as a single member with two separate internal cavities, with pawl 160 being molded to the portion between the two internal cavities.

First ends of resilient members, depicted in the figures as springs 174 and 176, are attached to pawl 160 adjacent distal end 160*a*. Second ends of springs 174 and 176 are secured to shroud 178, which comprises first portion 148*a* of band 148, and which covers and contains actuators 150 and 152. Springs 174 and 176 maintain pawl 160 generally perpendicular to ratchet 162, which is carried by second portion 148*b*. Relative longitudinal movement between first portion 148*a* and second portion 148*b* effects the change in the size of opening 180, as can been seen in FIGS. 9 and 11. Springs 174 and 176 provide a counterbalanced load at distal end 160*a* of pawl 160 which, in the absence of a force exerted by extension of either actuator 150 or 152 due to actuation, is sufficient to maintain angle 170 engaged in one of notches 172 to prevent relative movement between first portion 148*a* and second portion 148*b*, maintaining the selected size of area 180.

Figure 11:
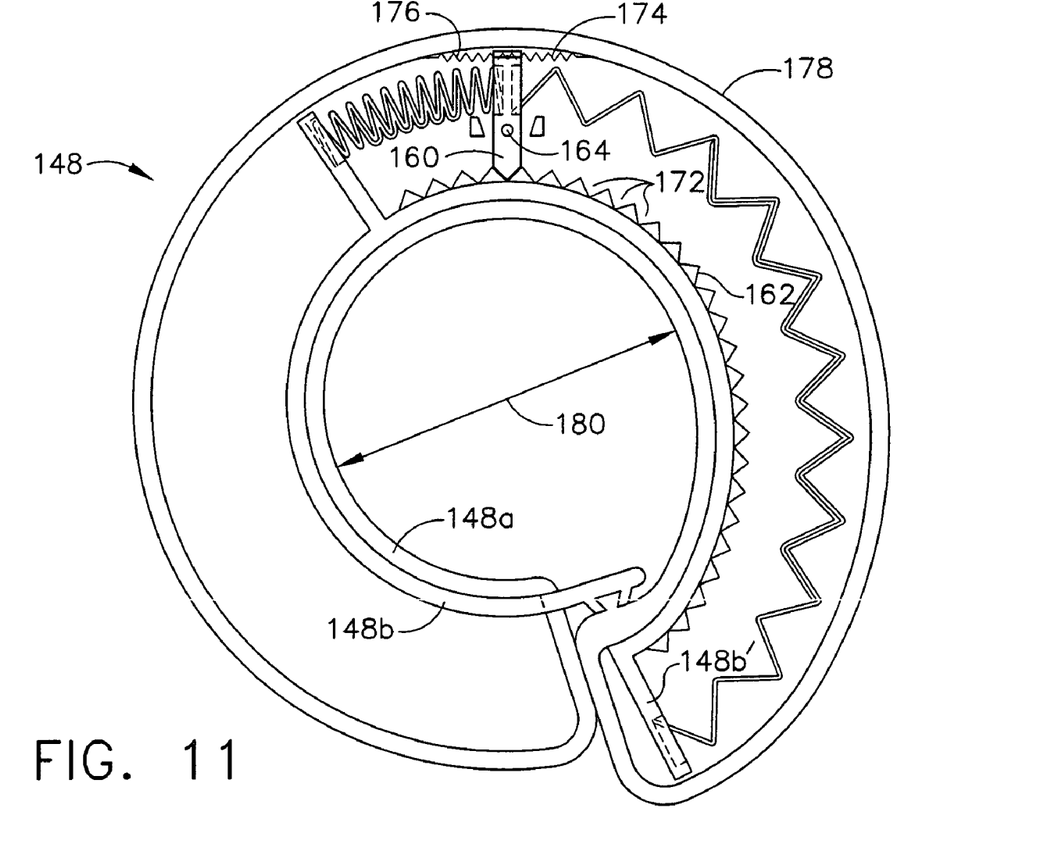
FIG. 11 is a plan view of the band of FIG. 9, depicting the minimum area configuration.
Figure 12:
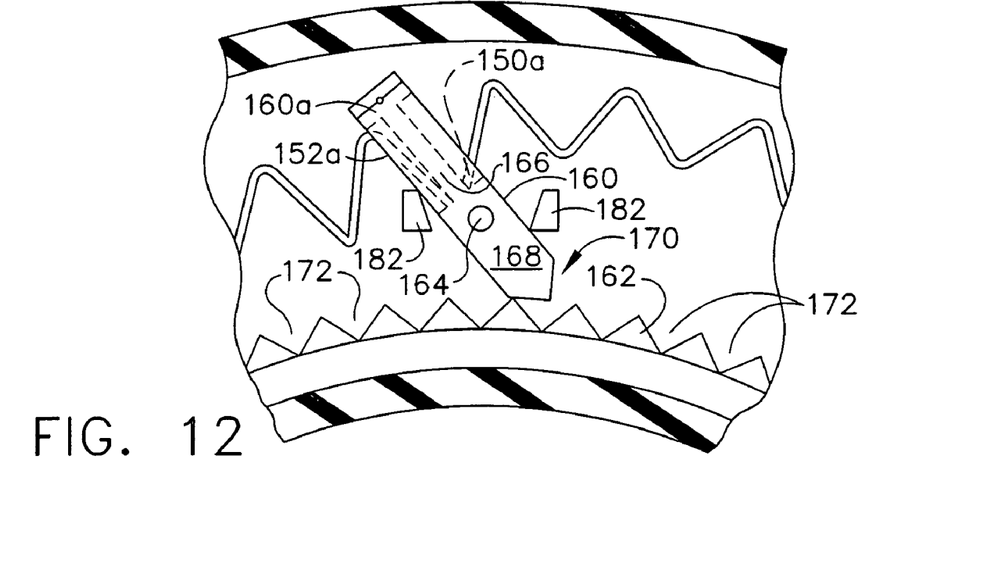
FIG. 12 is an enlarged, fragmentary side view of the ratchet and pawl of the band of FIG. 9.

To adjust the size of area 180, and thusly the stoma size. either actuator 150 or 152 is actuated. In the embodiment depicted, to reduce the size of area 180, actuator 150 is actuated, as seen in FIG. 11. As seen in FIGS. 11 and 12, when actuator 150 is actuated, shroud 178 restrains outward movement of actuator 150, resulting in end 150*a* urging against upper portion 166, rotating pawl 160 counter clockwise and disengaging angle 170 from notches 172. Stops 182 prevent excessive rotation of pawl 160 in either direction, while allowing sufficient rotation for pawl 160 to disengage ratchet 162. As actuator 150 extends in length, and pawl 160 disengages ratchet 162, first and second portions 148*a* and 148*b* may move relative to each other.

Second end 150*b* of actuator 150 is connected to distal end 148*b'* of second portion 148*b*. Upon disengagement of pawl 162, actuator 150 urges distal end 148*b'* clockwise in FIGS. 9 and first portion 148*a*, via the force exerted on pawl 160 through pivot 164 to shroud 178, counterclockwise, increasing the amount of overlap between first portion 148*a* and second portion 148*b*, reducing the size of area 180. When the desired size of area 180 is reached, element 154 is deactivated, and when the pressure of the medium within actuator 150 drops sufficiently, pawl 160 reengages ratchet 162, thereby maintaining the desired size of area 180.

In positions where one actuator is compressed and the other actuator is extended, such as seen in FIG. 11, springs 174 and 176 are sufficient to overcome any moment on pawl 160 created by unactuated actuators 150 and 152, and maintain pawl 160 in engagement with ratchet 162.

Self contained actuators 150 and 152. are not limited to use with the configuration of band 148, nor is band 148 limited to use with self contained actuators.

Figure 13:
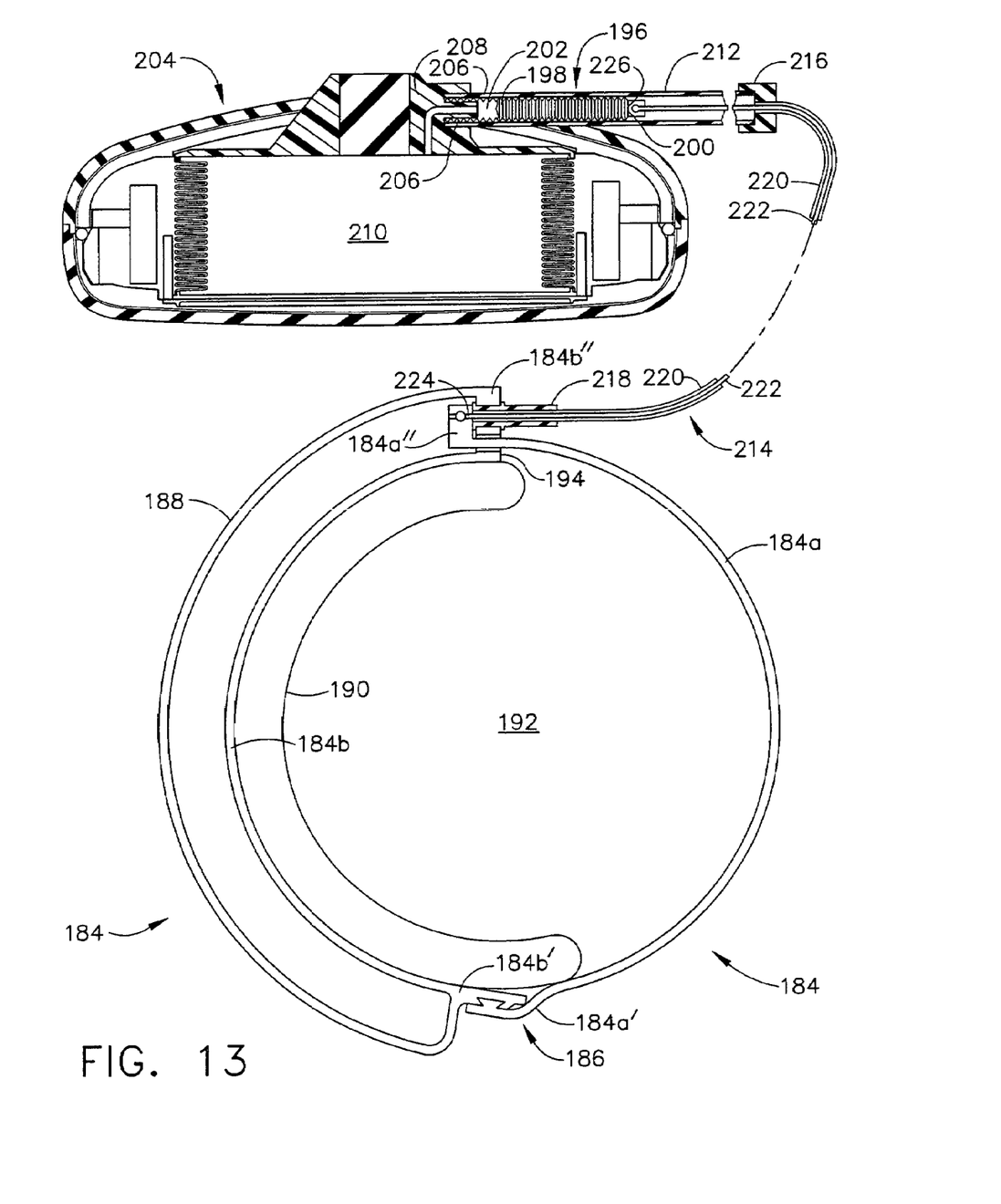
FIG. 13 illustrates another embodiment of an adjustable band, shown in plan view, with another embodiment of an actuator.

FIG. 13 illustrates another embodiment of an actuator, in conjunction with another embodiment of an adjustable band. Band 184 includes first portion 184*a* and second portion 184*b*, with each portion having attachment mechanism 186 which may be used to connect ends 184*a'* and 184*b'* together after band 184 has been disposed about an anatomical feature. Although attachment mechanism 186 is depicted as having a transverse dove tail configuration, any attachment mechanism may be used. Second portion 184*b* includes a shroud 188 which encloses end 184*a"* throughout its travel, as described below.

Band 184 is comprised of any suitable biocompatible material having sufficient resilience, strength and fatigue resistance, such as implant grade silicone. The inner surface may be of any suitable configuration which does irritate or damage adjacent tissue, such as for example, as shown in U.S. Provisional Patent Application Ser. No. 60/530,497, filed Dec. 17, 2003, for Mechanically Adjustable Gastric Band, which is incorporated by reference. Second portion 184*b* may have a balloon 190 disposed on its inner surface, which is depicted as extending past attachment mechanism 186. Balloon 190 may have a fixed volume. It is noted that, in the embodiment depicted, the inner surface of first portion 184*a* does not have a similar feature. As illustrated in FIG. 13, band 184 is at its largest size, encircling area 192, having a diameter of approximately 1.35 inches, for example only. At its smallest size, when end 184*a"* has traveled its full distance within shroud 188, most of. first portion 184*a* is disposed within shroud 188, the ends of balloon 190 are proximal each other and area 192 has a diameter of about 0.71 inches. (It is noted that although area 192 is depicted as generally circular and is referred to as having a diameter, area 192 is not limited to a circle or circular shape.) Thus, in the embodiment depicted, first portion 184*a* must be small enough to move through opening 194, and the inner surface of first portion 184*a* should not have any features, such as a balloon, which would interfere with such movement.

Actuator 196 is depicted as comprising generally cylindrical bellows 198, which is illustrated as a corrugated member having a series of folds creating spaced apart circular ridges. Although the ridges and folds are illustrated as being parallel, and evenly shaped and spaced, they are not required to be. Bellows may be made from any suitable biocompatible material, such as titanium which is MRI safe. Bellows 198 is closed at end 200, defining internal cavity 202. Internal cavity 202 may be in fluid communication with a source of fluid, which may be a remotely operated bidirectional infuser 204, similar to infuser 64, or any other fluid source capable of repetitively bidirectionally moving fluid. In the embodiment depicted, end 206 of bellows 198 is secured to housing 208 of bidirectional infuser 204, placing internal cavity 202 in fluid communication with variable internal volume 210. In the embodiment depicted, the fluid within internal cavity 202 and internal volume 210 may be saline solution. Movement of bellows 198 is constrained to be longitudinal by bellows housing 212, which is secured to housing 208.

Drive cable assembly 214 is provided between bellows housing 212 and band 184. Cable drive assembly 214 includes fitting 216, which is secured to bellows housing 212, and fitting 218, which is secured to end 184b''', each being secured in any suitable manner. Sheath 220 extends between fittings 216 and 218, providing a mechanical ground for cable 222 disposed therein. Cable end 224 is secured to end 184a''', and cable end 226 is secured to bellows end 200, each being secured in any suitable manner.

To actuate actuator 196, fluid from internal volume 210 is forced through fluid port 228, lengthening bellows 198. As a result of the relative cross sectional areas of bellows 198 and internal volume 210, bellows 198 acts as an amplifier, with a small amount of fluid producing the longitudinal expansion required to adjust the size of band 184. As end 200 moves within bellows housing 212, cable end 224 moves band end 184a''' within shroud 188 relative to portion 184b, thereby decreasing the size of the stoma created by band 184. To increase the size of the stoma, fluid is withdrawn from bellows 198, retracting cable 222, moving end 184a''' toward end 184b'''.

Cable assembly 214 may be made of any suitable biocompatible material. Cable end 224 needs to be sufficiently stiff to push end 184a''' within shroud 188 the desired distance. Shroud 188 protects surrounding tissue from the movement of end 184a''', and also constrains the movement of cable end 224 and cable 222, functioning similarly to sheath 220, to produce the desired movement of end 184a'''.

Figure 14:
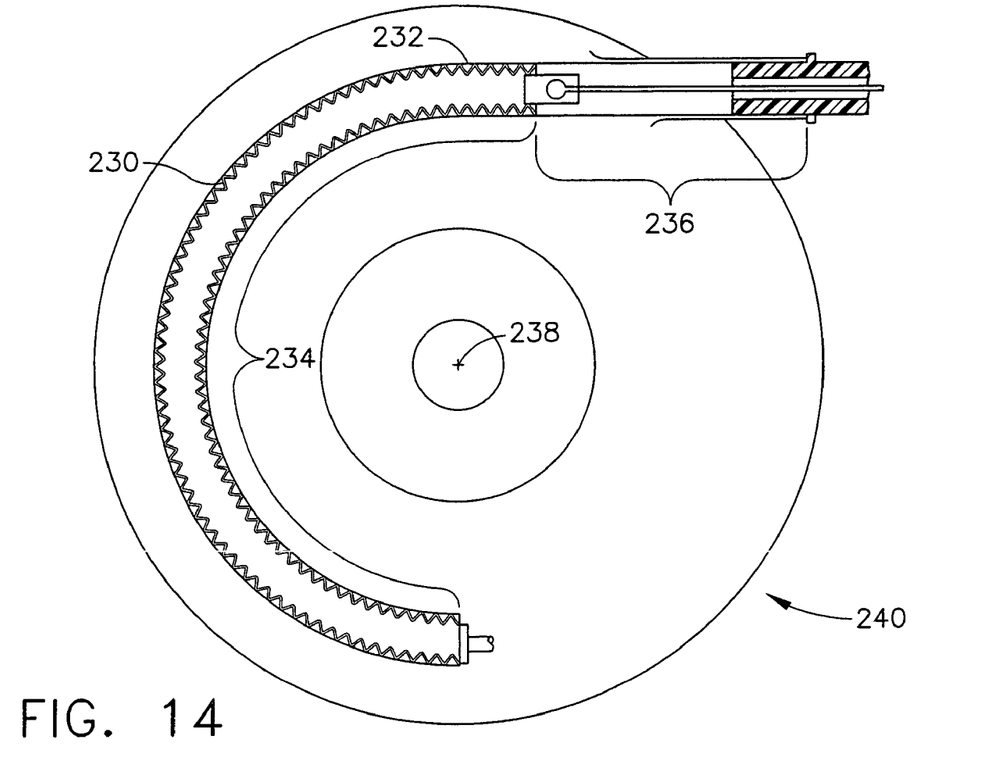
FIG. 14 is a top view of another embodiment of a bidirectional infuser.
Figure 15:
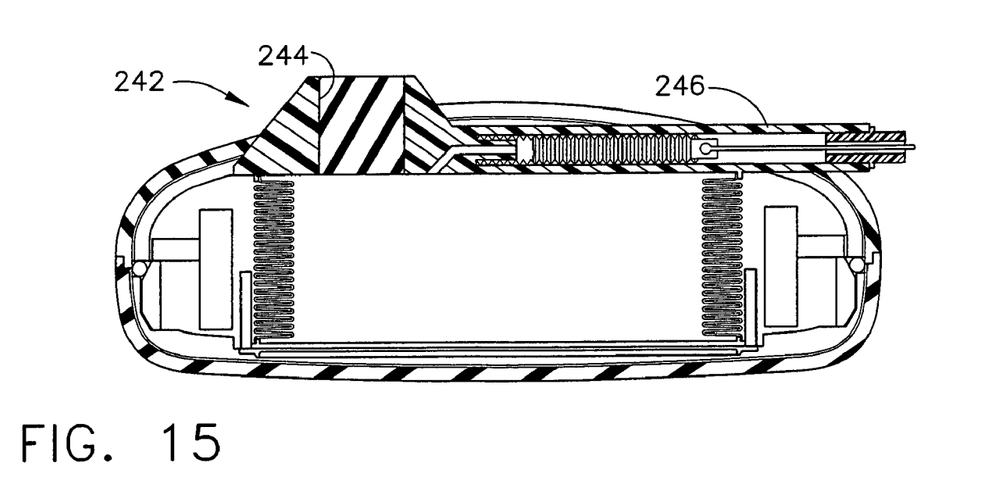
FIG. 15 is a side view in partial cross section of another embodiment of a bidirectional infuser.
Figure 16:
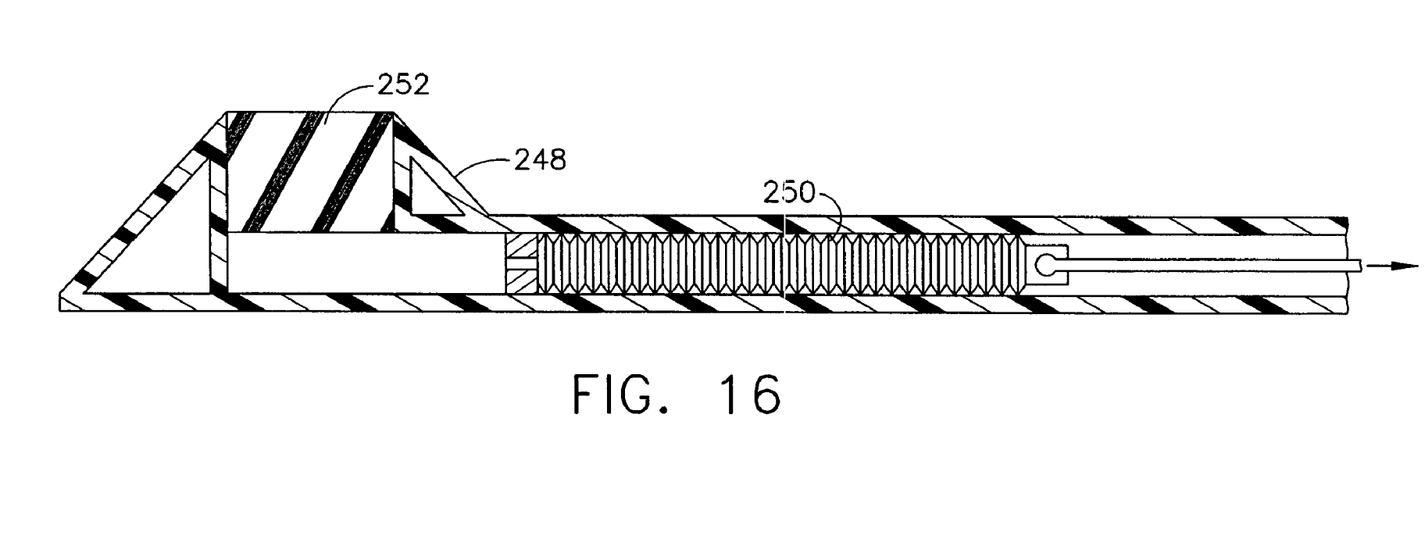
FIG. 16 is a side view of an injection port.

FIGS. 14, 15 and 16 illustrate alternate embodiments of bidirectional infusers showing alternate configurations of a bellows. FIG. 14 illustrates bellows 230 disposed within bellows housing 232 having arcuate portion 234. Bellows housing 232 may include straight section 236 as shown. The arcuate configuration allows the length of bellows housing 232 to be longer than the distance from center 238 while not extending very far beyond the circumference of bidirectional infuser 240, increasing the available stroke of bellows 230. Bellows housing 232 may be secured to infuser 240 in any suitable manner, or may be formed integrally therewith.

FIG. 15 illustrates bidirectional infuser 242 with septum 244 offset from the center of outer periphery of infuser 242. This allows the portion of bellows housing 246 overlying infuser 242 to be longer in comparison to bidirectional infuser 204 which has a centrally disposed septum.

FIG. 16 illustrates injection port 248 with bellows 250. To actuate bellows 250, fluid is injected or withdrawn via septum 252.

As mentioned above, the components of embodiments constructed according to the teachings of the invention may be made of non-ferromagnetic materials, allowing the patient to under go Magnetic Resonance Imaging (MRI) without damage to the device or patient. Being MRI safe avoids limiting the medical procedures which are safely available to patients having implanted bands, actuators, infusers or injection ports.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims submitted herewith.

What is claimed is:

1. An assembly for treatment of a medical condition comprising:
   (a) an actuator assembly, wherein said actuator assembly is configured for implantation;
   (b) an extensible implantable band, said extensible implantable band having first and second ends and an external surface, wherein said extensible implantable band is associated with said actuator assembly, wherein the extensible implantable band is sized and configured to fit around a portion of a human patient's stomach, wherein the external surface of the extensible implantable band defines an inner opening; and
   (c) an extensible actuator, said extensible actuator comprising
      (i) first and second ends, and
      (ii) at least one sidewall extending between said first and second ends, said at least one sidewall defining a reference axis in a longitudinally extended position;
   said first and second ends of said extensible actuator defining a first length therebetween along said reference axis when said extensible actuator is retracted to a longitudinally retracted position;
   said first and second ends of said extensible actuator defining a second length therebetween along said reference axis when said extensible actuator is expanded to a longitudinally extended position, wherein the second length is greater than the first length;
   wherein the first end of the extensible actuator is secured adjacent to the first end of the extensible implantable band, wherein the second end of the extensible actuator is secured adjacent to the second end of the extensible implantable band, wherein said extensible actuator is configured to expand from said first length to said second length to effect changes in said extensible implantable band, such that the size of the inner opening increases as the extensible actuator expands, and such that the size of the inner opening decreases as the extensible actuator retracts.

2. The assembly of claim 1, wherein said extensible actuator comprises a series of folds and spaced apart ridges.

3. The assembly of claim 1, wherein said first and second ends of said extensible actuator are in direct contact with said extensible implantable band at spaced apart locations.

4. The assembly of claim 1, wherein said extensible actuator is disposed at least partially within said extensible implantable band.

5. The assembly of claim 1, wherein said extensible actuator comprises an internal cavity connectable to a source of a fluid, wherein changes in fluid delivery transition said extensible actuator from said first length to said second length.

6. The assembly of claim 1, wherein said extensible actuator comprises an internal cavity that is completely sealed.

7. The assembly of claim 1, further comprising a thermal element configured to transition said extensible actuator from said first length to said second length.

8. The assembly of claim 7, wherein said thermal element comprises a Peltier thermoelectric device.

9. The assembly of claim 7, wherein said thermal element comprises a thin film heater.

10. The assembly of claim 1, comprising a clutch mechanism configured to hold an effective inner perimeter of said extensible implantable band at a desired size.

11. The assembly of claim 10, wherein said clutch mechanism comprises a ratchet and pawl.

12. The assembly of claim 1, wherein transitioning said extensible actuator from said first length to said second length decreases an effective inner perimeter of said extensible implantable band.

13. The assembly of claim 1, wherein transitioning said extensible actuator from said first length to said second length increases an effective inner perimeter of said extensible implantable band.

14. The assembly of claim 1, wherein said extensible implantable band is connected to a bidirectional flow device.

15. The assembly of claim 14, wherein said bidirectional flow device comprises a bellows accumulator having an internal accumulator volume, said accumulator and said extensible actuator being configured such that a small change in the internal accumulator volume produces a large change in length.

16. The assembly of claim 1, wherein said extensible actuator is configured to transition from said first length to said second length with a transition element selected from the group consisting of a thermal element, a thermoelectric device, a Peltier device, a thin film heater, an internal cavity having a variable volume and a variable pressure responsive to fluid delivery, an internal cavity having a static volume and a variable pressure responsive to fluid delivery, a hydraulic device, and combinations thereof.

17. An assembly for treatment of a medical condition comprising:
(a) an actuator assembly, wherein said actuator assembly is configured for implantation;
(b) an extensible implantable band having first and second ends and an external surface, wherein said extensible implantable band is associated with said actuator assembly, wherein the extensible implantable band has an interior, wherein the external surface of the extensible implantable band defines an inner opening;
(c) a first actuator positioned within the interior of the extensible implantable band, said first actuator associated with said extensible implantable band, said first actuator comprising;
  (i) first and second ends, and
  (ii) a first extensible body, said first extensible body configured to change length; and
(d) a second actuator positioned within the interior of the extensible implantable band, said second actuator associated with said extensible implantable band, wherein said second actuator is configured to be actuated independently from said first actuator, wherein the first and second actuators are opposingly positioned relative to each other within the interior of the extensible implantable band, said second actuator comprising;
  (i) first and second ends, and
  (ii) a second extensible body, said second extensible body configured to change length, wherein changing the length of said first actuator and said second actuator adjusts said extensible implantable band;
wherein the first and second actuators are operable such that the size of the inner opening increases when the first extensible body increases in length while the second extensible body decreases in length;
wherein the first and second actuators are further operable such that the size of the inner opening decreases when the second extensible body increases in length while the first extensible body decreases in length.

18. The assembly of claim 17, where increasing the length of said first actuator increases an inner diameter of said extensible implantable band and increasing the length of said second actuator decreases said inner diameter of said extensible implantable band.

19. An assembly for treatment of a medical condition comprising:
(a) an actuator assembly, said actuator configured for implantation, wherein said actuator assembly incorporates fluid-based actuation, wherein the actuator assembly defines a fluid reservoir having an adjustable volume;
(b) an extensible implantable band associated with said actuator assembly, the extensible implantable band comprising;
  (i) first and second ends,
  (ii) an attachment mechanism, wherein said attachment mechanism is configured to join said first and second ends, and
  (iii) an actuator, wherein the actuator is configured to adjust an inner diameter of said extensible implantable band after said first and second ends have been joined, wherein the actuator comprises a drive cable having a first end and a second end, wherein the first end of the drive cable is fixedly coupled with a first portion of the extensible implantable band, wherein the second end of the drive cable is coupled with the actuator assembly, such that the drive cable extends from the extensible implantable band to the actuator assembly, wherein the first portion of the extensible implantable band is movable relative to a second portion of the implantable band, wherein the actuator is operable to translationally drive the drive cable to change an internal perimeter defined by the extensible implantable band after said first and second ends of the extensible implantable band have been joined, wherein the actuator assembly is operable to translationally drive the drive cable by adjusting the fluid volume of the reservoir; and
(c) a balloon, said balloon being affixed to the inner diameter of said extensible implantable band.

20. The assembly of claim 19, wherein the balloon has a fixed volume.

* * * * *